US010575946B2

(12) United States Patent
Costello et al.

(10) Patent No.: US 10,575,946 B2
(45) Date of Patent: Mar. 3, 2020

(54) HEART VALVE PROSTHESIS AND SEPARATE SUPPORT FLANGE FOR ATTACHMENT THERETO

(71) Applicant: Medtronic Vascular, Inc., Santa Rosa, CA (US)

(72) Inventors: Declan Costello, County Mayo (IE); Donna Curley, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 504 days.

(21) Appl. No.: 15/253,933

(22) Filed: Sep. 1, 2016

(65) Prior Publication Data

US 2018/0055633 A1 Mar. 1, 2018

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2210/0014* (2013.01); *A61F 2310/00017* (2013.01); *A61F 2310/00023* (2013.01); *A61F 2310/00029* (2013.01); *A61F 2310/00071* (2013.01)

(58) Field of Classification Search
CPC ........ A61F 2/24; A61F 2/2409; A61F 2/2412; A61F 2/2418; A61F 2/2427; A61F 2/2433; A61F 2/2436; A61F 2/2442; A61F 2220/0008; A61F 2220/0016
See application file for complete search history.

(56) References Cited

U.S. PATENT DOCUMENTS

| 5,458,639 | A | 10/1995 | Tsukashima et al. |
| 5,957,949 | A | 9/1999 | Leonhardt et al. |
| 6,500,147 | B2 | 12/2002 | Omaleki et al. |
| 6,554,795 | B2 | 4/2003 | Bagaoisan et al. |
| 6,676,692 | B2 | 1/2004 | Rabkin et al. |
| 6,736,827 | B1 | 5/2004 | McAndrew et al. |

(Continued)

FOREIGN PATENT DOCUMENTS

WO WO2009/045331 4/2009

OTHER PUBLICATIONS

PCT/US2017/049875, The International Search Report and the Written Opinion of the International Searching Authority, dated Nov. 16, 2017, 14pgs.

*Primary Examiner* — Robert A Lynch
(74) *Attorney, Agent, or Firm* — Medler Ferro Woodhouse & Mills PLLC

(57) ABSTRACT

A valve prosthesis assembly for implantation into a native valve site includes a valve prosthesis with a prosthetic valve component and a frame. The frame of the valve prosthesis includes a central portion supporting the prosthetic valve component, the central portion being configured to fit within an annulus of the native valve site, and an inflow portion configured to engage an upstream side of the annulus and restrict movement of the valve prosthesis in a downstream direction of blood flow at the native valve site. The valve prosthesis assembly also includes a separate support flange configured to be attached to the frame after the valve prosthesis has been deployed in situ and a plurality of anchors configured to attach the support flange to the frame and configured to embed into the annulus to anchor the frame of the valve prosthesis to the native valve.

20 Claims, 13 Drawing Sheets

(56) References Cited

U.S. PATENT DOCUMENTS

| | | |
|---|---|---|
| 7,258,696 B2 | 8/2007 | Rabkin et al. |
| 7,276,078 B2 | 10/2007 | Spenser et al. |
| 7,780,725 B2 | 8/2010 | Haug et al. |
| 8,083,732 B2 | 12/2011 | Arless et al. |
| 2003/0171773 A1 | 9/2003 | Carrison |
| 2003/0199963 A1 | 10/2003 | Tower et al. |
| 2003/0199971 A1 | 10/2003 | Tower et al. |
| 2004/0111111 A1 | 6/2004 | Lin |
| 2004/0210305 A1* | 10/2004 | Shu ............ A61F 2/2409 623/2.11 |
| 2007/0293944 A1 | 12/2007 | Spenser |
| 2008/0077234 A1 | 3/2008 | Styrc |
| 2008/0243245 A1 | 10/2008 | Thambar |
| 2009/0099653 A1 | 4/2009 | Suri et al. |
| 2010/0161036 A1 | 6/2010 | Pintor et al. |
| 2010/0168844 A1 | 7/2010 | Toomes et al. |
| 2010/0185274 A1 | 7/2010 | Moaddeb et al. |
| 2010/0211165 A1* | 8/2010 | Schreck ............ A61F 2/2418 623/2.18 |
| 2010/0280595 A1 | 11/2010 | Bilge et al. |
| 2011/0054466 A1 | 3/2011 | Rothstein et al. |
| 2011/0098802 A1 | 4/2011 | Braido et al. |
| 2011/0172765 A1 | 7/2011 | Nguyen et al. |
| 2011/0208297 A1 | 8/2011 | Tuval et al. |
| 2011/0224785 A1 | 9/2011 | Hacohen |
| 2011/0264206 A1 | 10/2011 | Tabor |
| 2012/0022639 A1 | 1/2012 | Hacohen et al. |
| 2012/0022640 A1 | 1/2012 | Gross et al. |
| 2012/0035722 A1 | 2/2012 | Tuval |
| 2012/0052040 A1 | 3/2012 | Hunter et al. |
| 2012/0101572 A1 | 4/2012 | Kovalsky et al. |
| 2013/0035759 A1 | 2/2013 | Gross et al. |
| 2013/0317418 A1 | 11/2013 | Freyman et al. |
| 2014/0018910 A1 | 1/2014 | Moaddeb et al. |
| 2014/0207231 A1* | 7/2014 | Hacohen ............ A61F 2/2427 623/2.11 |
| 2014/0214157 A1 | 7/2014 | Bortlein et al. |
| 2014/0271533 A1 | 9/2014 | Freyman et al. |
| 2014/0277411 A1* | 9/2014 | Bortlein ............ A61F 2/24 623/2.11 |
| 2015/0012085 A1 | 1/2015 | Salahieh et al. |

* cited by examiner

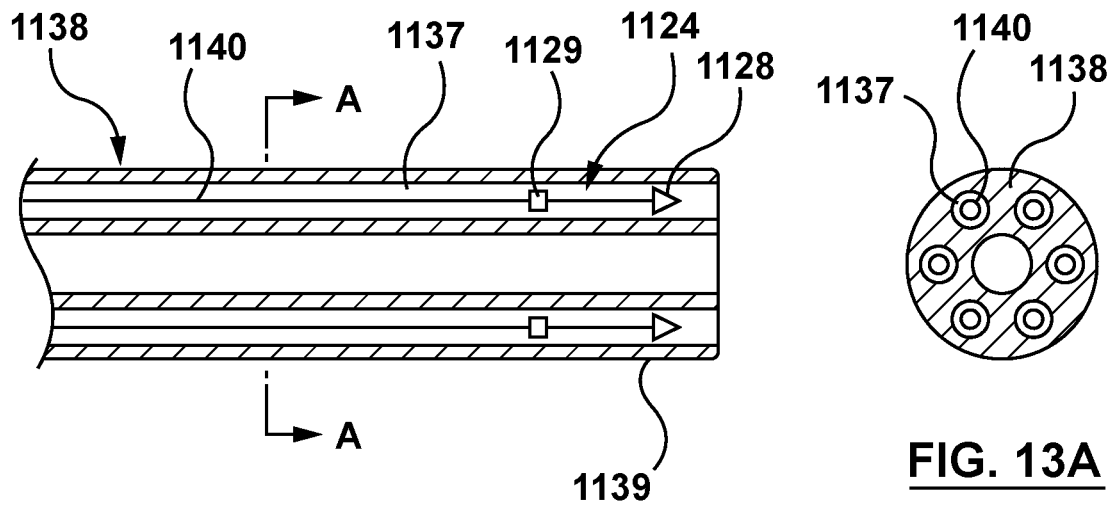
FIG. 13
FIG. 13A
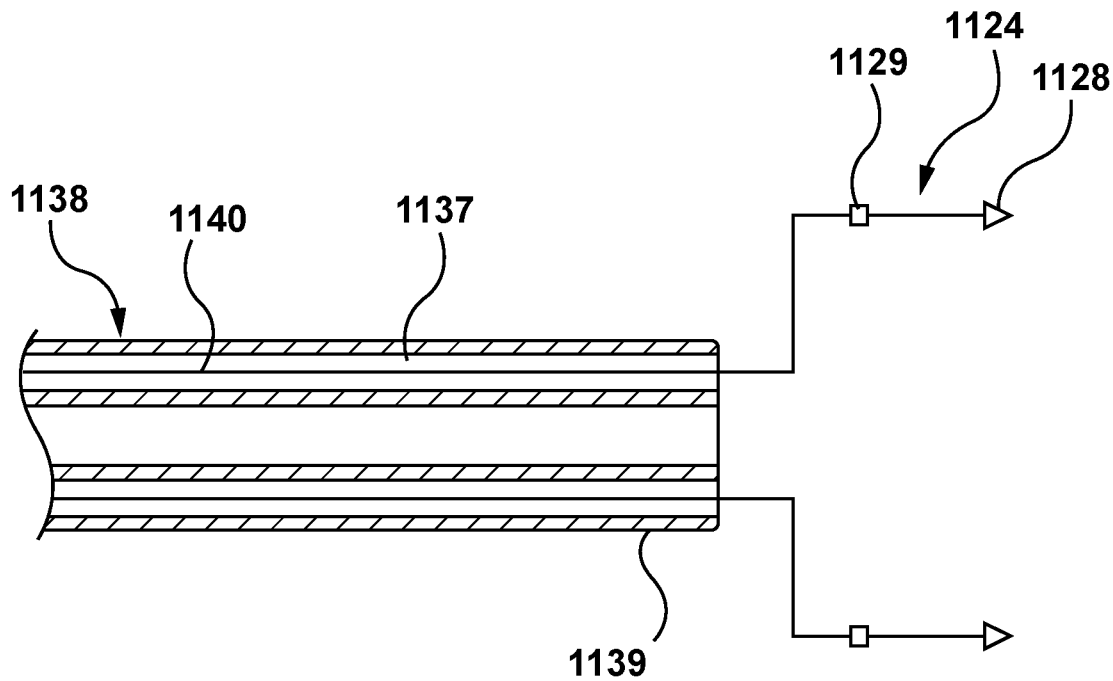
FIG. 14

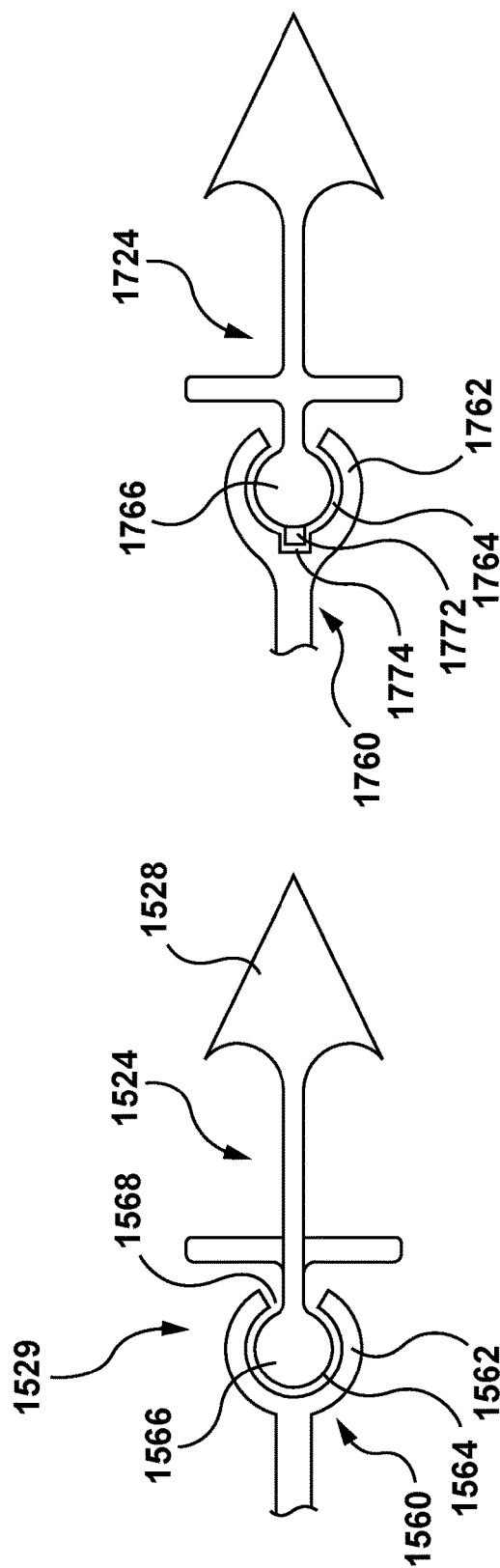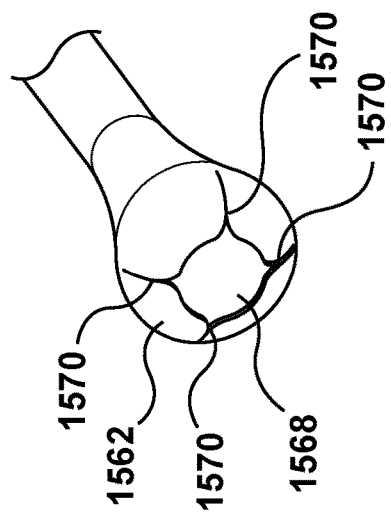
FIG. 17
FIG. 16
FIG. 15

HEART VALVE PROSTHESIS AND SEPARATE SUPPORT FLANGE FOR ATTACHMENT THERETO

FIELD OF THE INVENTION

The invention relates to transcatheter valve prostheses and methods of repairing and/or preventing paravalvular leakage after implantation thereof. More specifically, the present invention relates to a support flange which is deployed after implantation of a valve prosthesis.

BACKGROUND OF THE INVENTION

A wide range of medical treatments are known that utilize "endoluminal prostheses." As used herein, endoluminal prostheses are intended to include medical devices that are adapted for temporary or permanent implantation within a body lumen, including both naturally occurring and artificially made lumens. Examples of lumens in which endoluminal prostheses may be implanted include but are not limited to arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a delivery catheter or by crimping onto a balloon catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent," which is incorporated by reference herein in its entirety.

A human heart includes two atrio-ventricular valves through which blood flows from the atria to the ventricles, the valves functioning to prevent return of blood to the atrium. The tricuspid valve, also known as the right atrio-ventricular valve, is a tri-flap valve located between the right atrium and the right ventricle. The mitral valve, also known as the bicuspid or left atrioventricular valve, is a dual-flap valve located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function. The mitral valve includes two moveable leaflets, an anterior leaflet and a posterior leaflet, that each open and close in response to differential pressures on either side of the valve. Ideally, the leaflets move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with mitral regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Embodiments hereof are related to a devices for and methods of preventing and/or repairing leakage between the valve prosthesis and native valve tissue.

BRIEF SUMMARY OF THE INVENTION

Embodiments hereof are directed to a valve prosthesis assembly for implantation into a native valve site. The valve prosthesis assembly includes a valve prosthesis with a prosthetic valve component and a frame. The frame of the valve prosthesis includes a central portion supporting the prosthetic valve component, the central portion being configured to fit within an annulus of the native valve site, and an inflow portion configured to engage an upstream side of the annulus and restrict movement of the valve prosthesis in a downstream direction of blood flow at the native valve site. The valve prosthesis assembly also includes a separate support flange configured to be attached to the frame after the valve prosthesis has been deployed in situ and a plurality of anchors configured to attach the support flange to the frame and configured to embed into the annulus to anchor the frame of the valve prosthesis to the native valve.

Embodiments hereof are also directed to a valve prosthesis assembly for implantation into a native valve site. The valve prosthesis assembly includes a valve prosthesis having a compressed configuration for delivery within a vasculature and a radially expanded configuration for deployment within an annulus of the native valve site. The valve prosthesis includes a prosthetic valve component and a frame. The frame includes a central portion supporting the prosthetic valve component, the central portion configured to fit within the annulus when the valve prosthesis is in the radially expanded configuration, and an inflow portion having a larger diameter than the central portion when the valve prosthesis is in the radially expanded configuration to engage an upstream side of the annulus and restrict movement of the valve prosthesis in a downstream direction of blood flow at the native valve site. The valve prosthesis assembly also includes a separate support flange configured to be attached to the frame after the valve prosthesis has been deployed in situ, the support flange having a compressed configuration for delivery within a vasculature and a radially expanded configuration for attachment to the frame. The support flange in the radially expanded configuration is a ring defining an opening therethrough and the support flange is formed from a shape memory material. The valve prosthesis assembly also includes a plurality of anchors configured to attach the support flange to the frame and configured to embed into the annulus to anchor the frame of the valve prosthesis to the native valve.

Embodiments hereof are also directed to a method of delivering and deploying a valve prosthesis assembly within a native valve. A valve prosthesis is advanced to the native valve. The valve prosthesis includes a prosthetic valve component coupled to a central portion of a frame. The valve prosthesis is deployed such that the central portion is disposed in the annulus of the native valve and an inflow portion having a larger diameter than the central portion engages an upstream side of the annulus to restrict movement of the valve prosthesis in a downstream direction of blood flow at the native valve. After the valve prosthesis has been deployed, a support flange is delivered to the native valve. The support flange is deployed, and the support flange is attached to the frame of the valve prosthesis with a plurality of anchors. The anchors are configured to embed into the annulus in order to anchor the frame of the valve prosthesis to the native valve.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 13 is a sectional side view of a distal end portion of an intermediate shaft of a delivery system for the support flange and the plurality of anchors of FIG. 11, wherein a plurality of radially expandable push wires and the plurality of anchors are housed within the intermediate shaft during delivery thereof and the intermediate shaft is removed from the delivery catheter in FIG. 13 for illustrative purposes only.

FIG. 13A is a cross-sectional view taken along line A-A of FIG. 13.

FIG. 14 is a sectional side view of the distal end portion of the intermediate shaft of FIG. 13, wherein the plurality of anchors are being deployed via the plurality of radially expandable push wires.

FIG. 15 is a side view of an anchor according to an embodiment hereof, wherein the anchor has a stopper or proximal end temporarily coupled to a distal end of its respective push wire via a ball and socket-type joint.

FIG. 16 is a perspective view of the socket of FIG. 15.

FIG. 17 is a side view of an anchor according to another embodiment hereof, wherein the anchor has a stopper or proximal end temporarily coupled to a distal end of its respective push wire via a ball and socket-type joint and the anchor is keyed to prevent rotation thereof.

DETAILED DESCRIPTION OF THE INVENTION

The following detailed description is merely exemplary in nature and is not intended to limit the invention or the application and uses of the invention. Although the description of embodiments hereof is in the context of mitral heart valve replacement, the invention may be adapted to be used for other valve replacement where it is deemed useful.

Furthermore, there is no intention to be bound by any expressed or implied theory presented in the preceding technical field, background, brief summary or the following detailed description.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Further the term "self-expanding" is used in the following description with reference to the frame of the valve prosthesis as well as components of the support flange and is intended to convey that the components are shaped or formed from a material that has a mechanical memory to return to an expanded deployed configuration from a compressed or constricted delivery configuration. Non-exhaustive exemplary materials that may be rendered self-expanding include stainless steel, a pseudo-elastic metal such as a nickel titanium alloy or nitinol, various polymers, and a so-called super alloy, which may have a base metal of nickel, cobalt, chromium, or other metal. Mechanical memory may be imparted to material used to form the frame by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Figure 1:
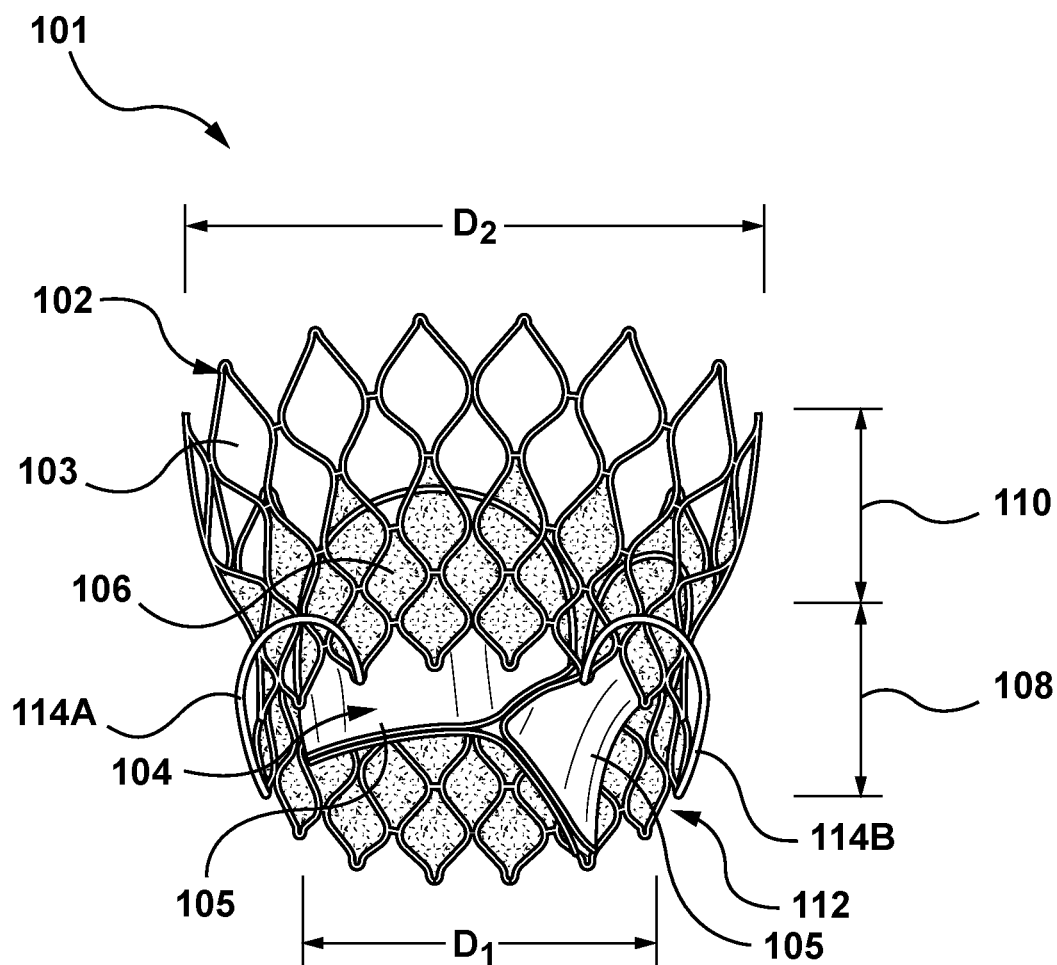
FIG. 1 is a perspective view of an exemplary transcatheter valve prosthesis for use in embodiments hereof.

Embodiments hereof are related to a valve prosthesis configured for deployment within a native heart valve of the heart in a transcatheter heart valve implantation procedure. FIG. 1 is a perspective view of an exemplary transcatheter valve prosthesis 101 for use in embodiments hereof, wherein the valve prosthesis is in an expanded, deployed configuration in accordance with an embodiment hereof. Valve prosthesis 101 is illustrated herein in order to facilitate description of the methods and devices to prevent and/or repair paravalvular leakage according to embodiments hereof. It is understood that any number of alternate heart valve prostheses can be used with the methods and devices described herein. Valve prosthesis 101 is merely exemplary and is similar to heart valve prostheses described in more detail in co-pending patent application, U.S. application Ser. No. 13/572,842 filed Aug. 13, 2012, herein incorporated by reference in its entirety, as well as U.S. Patent Application Publication Nos. 2012/0101572 to Kovalsky et al. and 2012/0035722 to Tuval, each of which are herein incorporated by reference in their entirety and illustrate heart valve prostheses configured for placement in a mitral valve.

Valve prosthesis 101 includes an expandable stent or frame 102 that supports a prosthetic valve component 104 within the interior of frame 102. Frame 102 is a unitary scaffold that may be a laser cut tubular stent defining cells or openings 103. As will be understood by one of ordinary skill in the art, the stent or frame of a valve prosthesis may have other configurations such as a series of sinusoidal patterned rings coupled to each other to form a self-expanding stent. In embodiments hereof, frame 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein. Alternatively, valve prosthesis 101 may be balloon-expandable as would be understood by one of ordinary skill in the art. Whether frame 102 is self-expanding or balloon-expandable, valve prosthesis 101 has a compressed configuration for delivery within a vasculature and a radially expanded configuration for deployment within an annulus of the native valve site.

In the embodiment depicted in FIG. 1, frame 102 of valve prosthesis 101 has a deployed stepped configuration including a first section or portion 108 having an expanded diameter $D_1$ and a second section or portion 110 having an expanded diameter $D_2$ which is greater than diameter $D_1$. Each portion of frame 102, i.e., first portion 108 and/or second portion 110, may be designed with a number of different configurations and sizes to meet the different requirements of the locations in which it may be implanted. When configured as a replacement for a mitral valve as described herein, enlarged second portion 110 functions as an inflow portion of valve prosthesis 101 and is positioned in the patient's left atrium, while first portion 108 functions as a central portion of valve prosthesis 101 that houses or supports prosthetic valve component 104 within the interior of frame 102. In such a mitral valve embodiment, first or central portion 108 is configured to fit within an annulus of the native valve site and an outflow end 112 extends into and anchors within the mitral annulus of a patient's left ventricle. Although the description of embodiments hereof are in the context of a valve prosthesis configured for implantation within a native mitral valve, embodiments hereof can also be used in other valves of the body, such as a valve prosthesis configured for implantation within a native tricuspid valve. Alternatively, valve prosthesis 101 may be configured as a replacement for an aortic valve, in which first portion 108 functions as an inflow end of valve prosthesis 101 and extends into and anchors within the aortic annulus of a patient's left ventricle, while second portion 110 functions as an outflow end of valve prosthesis 101 and is positioned in the patient's ascending aorta. Each portion of frame 102 may have the same or different cross-sections which may be for example circular, ellipsoidal, rectangular, hexagonal, square, or other polygonal shape, although at present it is believed that circular or ellipsoidal may be preferable when the valve prosthesis is being provided for replacement of the mitral or aortic valves. Frame 102 also includes two generally U-shaped support or positioning arms 114A, 114B which function to position and anchor valve prosthesis 101 at a native valve target site. Support arms 114A, 114B are described in more detail in co-pending patent application, U.S. application Ser. No. 13/572,842 filed Aug. 13, 2012, previously incorporated by reference, as well as U.S. Patent Application Publication Nos. 2012/0101572 to Kovalsky et al. and 2012/0035722 to Tuval, previously incorporated by reference. In one embodiment, support arms 114A, 114B are pressed or lay flat against frame 102 during delivery thereof and radially expand away from the stent during deployment. In another embodiment hereof, support arms 114A, 114B may distally extend from the distal end of the frame, i.e., outflow end 112, when in the compressed delivery configuration. During deployment, each support arm bends radially outward and then towards an outer surface of the stent such that it translates more than ninety degrees from the compressed configuration to proximally extend from the distal end of the stent when the stent is in the deployed configuration, as described in co-pending patent application, U.S. application Ser. No. 13/572,842 filed Aug. 13, 2012, previously incorporated by reference.

As previously mentioned, valve prosthesis 101 includes prosthetic valve component 104 within the interior of frame 102. Prosthetic valve component 104 is configured as a one-way valve to allow blood flow in one direction and thereby regulate blood flow there through. Prosthetic valve component 104 is capable of blocking flow in one direction to regulate flow there through via valve leaflets 105 that may form a bicuspid or tricuspid replacement valve. More particularly, if valve prosthesis 101 is configured for placement within a native valve having two leaflets such as the mitral valve, prosthetic valve component 104 includes two valve leaflets 105 to form a bicuspid replacement valve that closes with pressure on the outflow and opens with pressure on the inflow. In other embodiments in accordance herewith, the prosthetic valve component may be a tricuspid replacement valve or may be a single leaflet replacement valve. Valve leaflets 105 are sutured or otherwise securely and sealingly attached to an inner circumference of frame 102 and/or graft material 106 which encloses or lines frame 102 as would be known to one of ordinary skill in the art of prosthetic tissue valve construction. Referring to FIG. 1, leaflets 105 are attached along their bases to graft material 106, for example, using sutures or a suitable biocompatible adhesive.

Leaflets 105 may be made of pericardial material; however, the leaflets may instead be made of another material. Natural tissue for prosthetic valve leaflets for use in prosthetic valve component 104 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, Del., polyurethane, Gore-Tex or other cloth materials, nylon blends, polymeric materials, and vacuum deposition nitinol fabricated materials. One polymeric material from which the replacement valve leaflets can be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Delivery of valve prosthesis 101 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time the valve prosthesis 101 can be released from the delivery catheter and expanded in situ via self-expansion. The delivery catheter is then removed and valve prosthesis 101 remains deployed within the native target heart valve. Alternatively, valve prosthesis 101 may be balloon-expandable and delivery thereof may be accomplished via a balloon catheter as would be understood by one of ordinary skill in the art.

Figure 2:
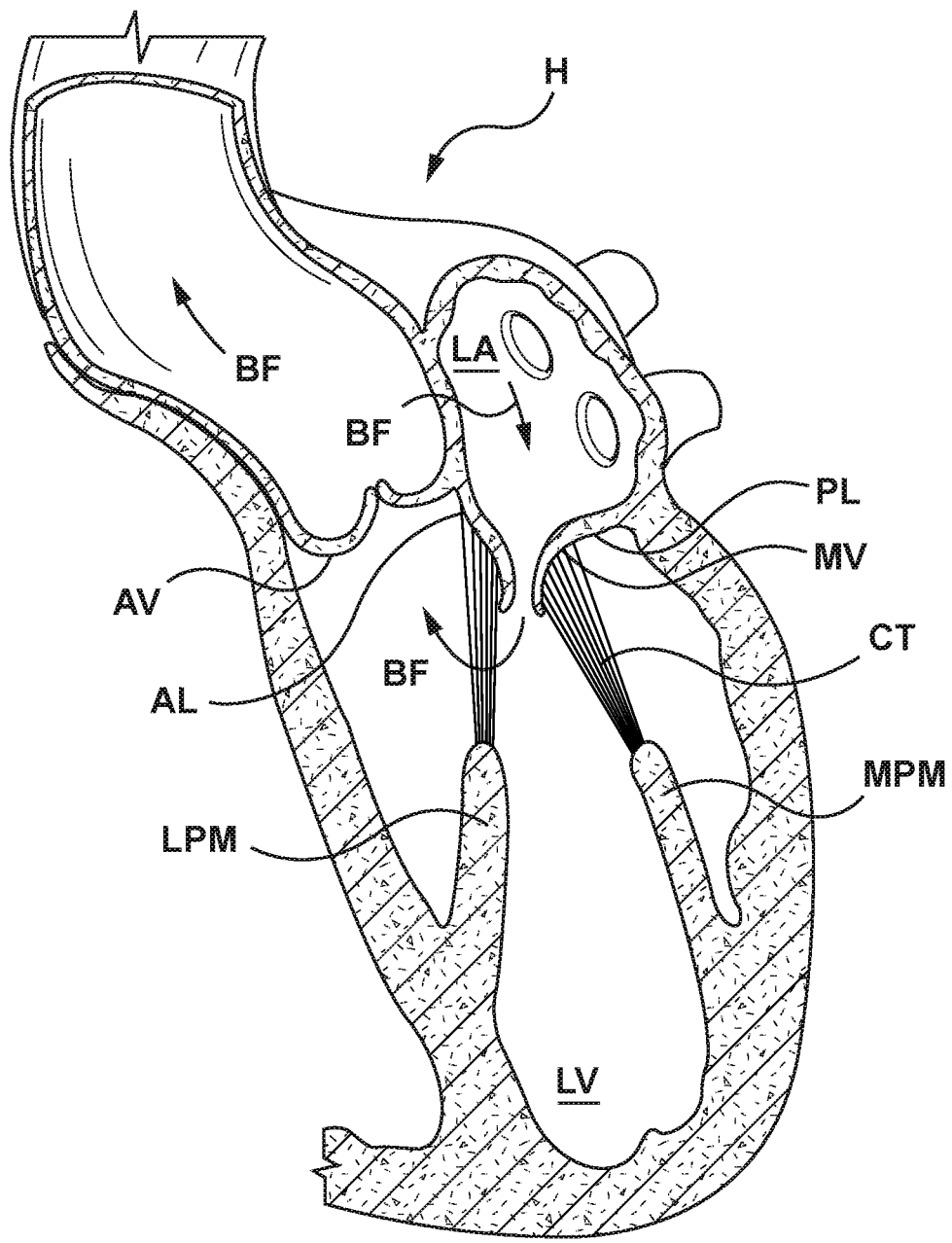
FIG. 2 is a side view illustration of the anatomy of a native mitral valve.

FIG. 2 illustrates a cross-sectional view of a heart H, the heart H includes a left atrium LA, a left ventricle LV, a mitral valve MV and an aortic valve AV. Blood flow BF is depicted with directional arrows in FIG. 2 in the left atrium LA, into left ventricle LV through mitral valve MV, and into the aorta through aortic valve AV. Mitral valve MV is saddle-shaped and includes two native leaflets, posterior leaflet PL and anterior leaflet AL, and chordae tendineae CT extend within the left ventricle LV between the native leaflets of the mitral valve MV and the papillary muscles. More particularly, chordae tendineae CT are cord-like tendons that connect the medial papillary muscle MPM to the posterior leaflet PL of the mitral valve MV and connect the lateral papillary muscle LPM to the anterior leaflet AL of the mitral valve MV. When the native mitral valve is operating properly, the native leaflets will generally function in such a way that blood flows toward the left ventricle LV when the leaflets are in an open position, and so that blood is prevented from moving toward the left atrium LA when the leaflets are in a closed position. During systole, when the native leaflets close to prevent backflow of blood into the atrium, the chordae tendineae CT assist in preventing the native leaflets from everting or prolapsing into the atrium by becoming tense and holding the native leaflets in the closed position.

Figure 3:
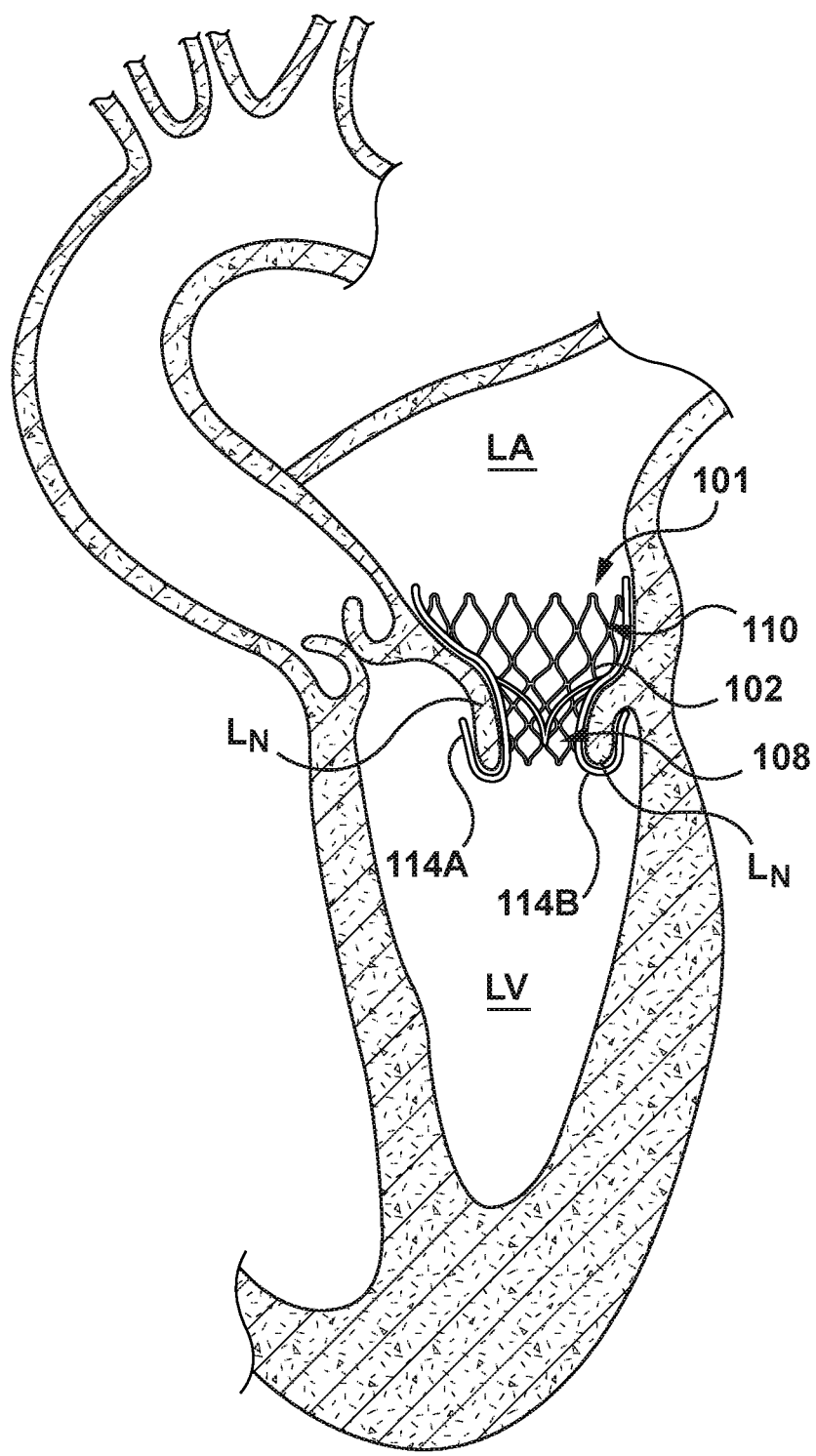
FIG. 3 is a side view illustration of the valve prosthesis of FIG. 1 implanted within a native valve annulus.

FIG. 3 is a side view illustration of valve prosthesis 101 implanted within a native mitral heart valve, which is shown in section, having native leaflets $L_N$. Valve prosthesis 101 is shown deployed within a native mitral valve, with first portion 108 extending into the left ventricle and enlarged second portion 110 extending into the left atrium. When valve prosthesis 101 is deployed within the valve annulus of a native heart valve, frame 102 expands within native valve leaflets $L_N$ of the patient's defective valve, retaining the native valve leaflets in a permanently open state. The native valve annulus may include surface irregularities on the inner surface thereof, and as a result one or more gaps or cavities/crevices may be present or may form between the perimeter of valve prosthesis 101 and the native valve annulus. For example, calcium deposits may be present on the native valve leaflets (e.g., stenotic valve leaflets) and/or shape differences may be present between the native heart valve annulus and prosthesis 101. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 4:
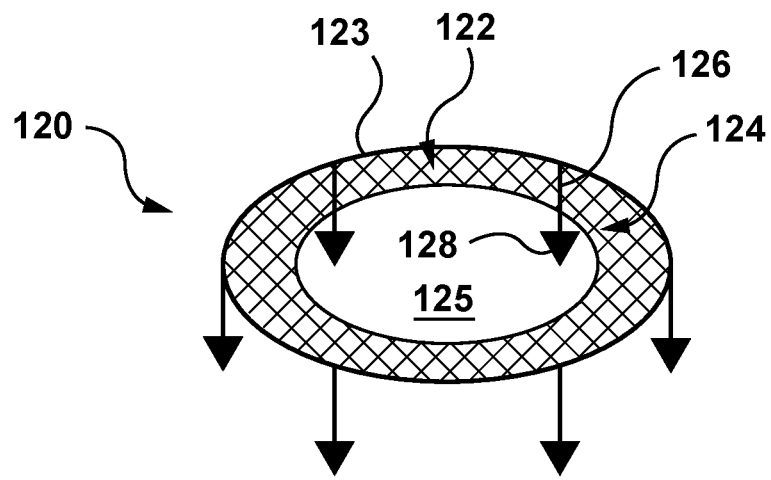
FIG. 4 is a perspective view of a support flange according to an embodiment hereof, wherein the support flange is configured to be attached to a valve prosthesis after the valve prosthesis has been deployed in situ and includes a plurality of anchors extending in an downstream direction.
Figure 5:
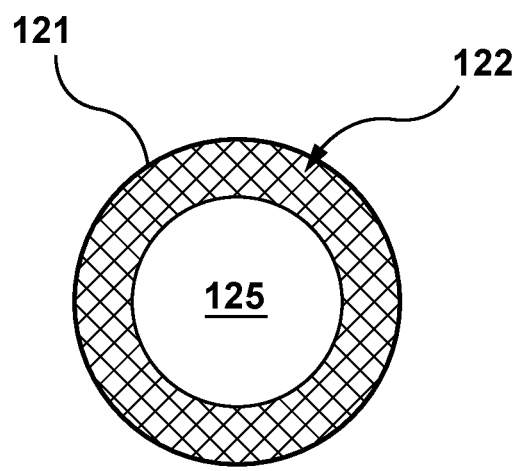
FIG. 5 is a top view of the support flange of FIG. 4.

Embodiments hereof are related to a separate support flange 120 configured to be attached to frame 102 after valve prosthesis 101 has been deployed in situ. More particularly, support flange 120 is deployed after implantation of valve prosthesis 101 to anchor the valve prosthesis and prevent leakage between the valve prosthesis and native valve tissue. When support flange 120 is attached to valve prosthesis 101 via a plurality of anchors 124, the support flange, the valve prosthesis, and the plurality of anchors form a valve prosthesis assembly 100 as best shown on FIG. 6C described herein. FIG. 4 is a perspective view of support flange 120 and FIG. 5 is a top view of the support flange of FIG. 4. Support flange 120 has a compressed configuration for delivery within a vasculature and a radially expanded configuration for attachment to frame 102 of valve prosthesis 101. Support flange 120 in the radially expanded configuration is an annular component 122 having an outer diameter and an inner diameter that defines a central opening 125 therethrough. In the configuration of FIGS. 4-5, annular component 122 has a mesh or lattice configuration with a plurality of diamond-shaped openings defined by the framework thereof, the diamond-shaped openings being shown by way of illustration and not limitation. Central opening 125 and the plurality of diamond-shaped openings are oriented transverse to blood flow when support flange 120 is deployed and implanted within the native heart valve. Annular component 122 is substantially planar. As utilized here, "substantially planar" includes a structure that has a flat profile with a minimal thickness. In an embodiment, the thickness may be in the range of 0.025 mm to 5 mm. Annular component 122 has an upstream surface 121 and an opposing downstream surface 123. Annular component 122 is formed from a shape memory or self-expanding material to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein.

Figure 9:
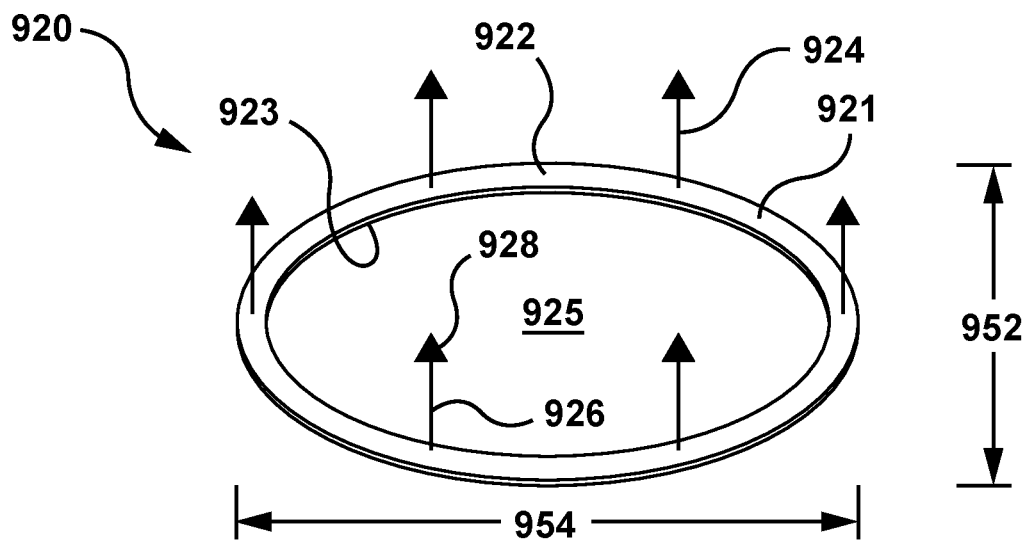
FIG. 9 is a perspective view of a support flange according to another embodiment hereof, wherein the support flange is configured to be attached to a valve prosthesis after the valve prosthesis has been deployed in situ and includes a plurality of anchors extending in an upstream direction.
Figure 10:
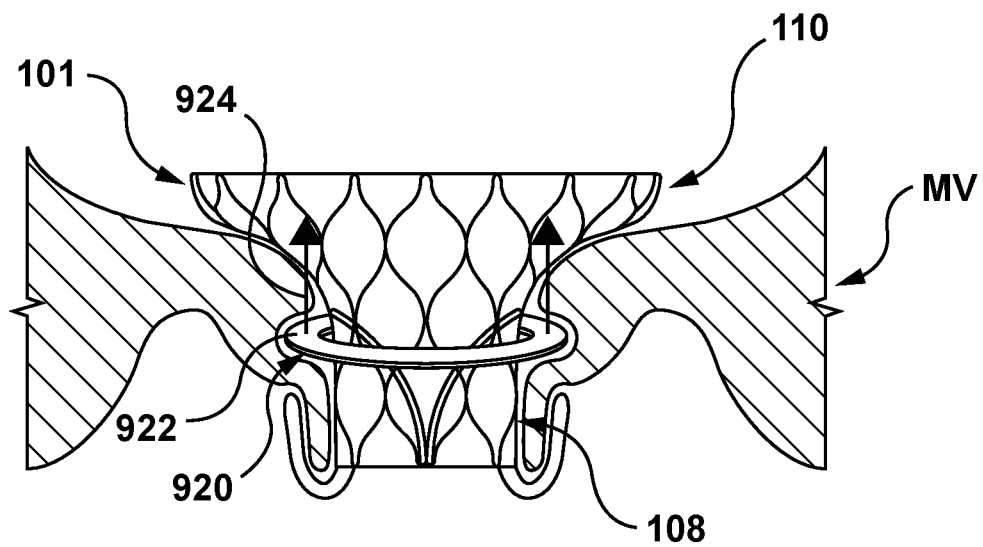
FIG. 10 is a side view illustrate of the support valve of FIG. 9 assembled or attached to a valve prosthesis in situ.

As shown in embodiments described herein, annular component 122 is not required to have a mesh or lattice configuration. For example, as shown in the embodiment of FIGS. 9-10 and the embodiment of FIGS. 11-12, the support flange may be a ring. Thus, although described as having a mesh or lattice configuration, annular component 122 in another embodiment hereof may be a radially compressible ring.

As previously stated, valve prosthesis assembly 100 also includes a plurality of anchors or pins 124 configured to attach support flange 120 to frame 102 of valve prosthesis 101 and configured to embed into the annulus to anchor frame 102 of valve prosthesis 101 to the native valve. In the embodiment of FIG. 4, the plurality of anchors 124 are attached to annular component 122 and extend in a downstream direction from downstream surface 123 of annular component 122. Each anchor 124 includes a shaft 126 with a pointed tip, barb or clip 128 at an unattached end thereof to embed or press into the native anatomy. Anchors 124 may be equally spaced around annular component 122 as shown in FIG. 4, or may be attached to annular component 122 in any other suitable pattern or spacing. Although shown with six anchors 124 circumferentially spaced apart around annular component 122, a greater number of anchors or a fewer number of anchors may be used depending upon application.

Figure 6A:
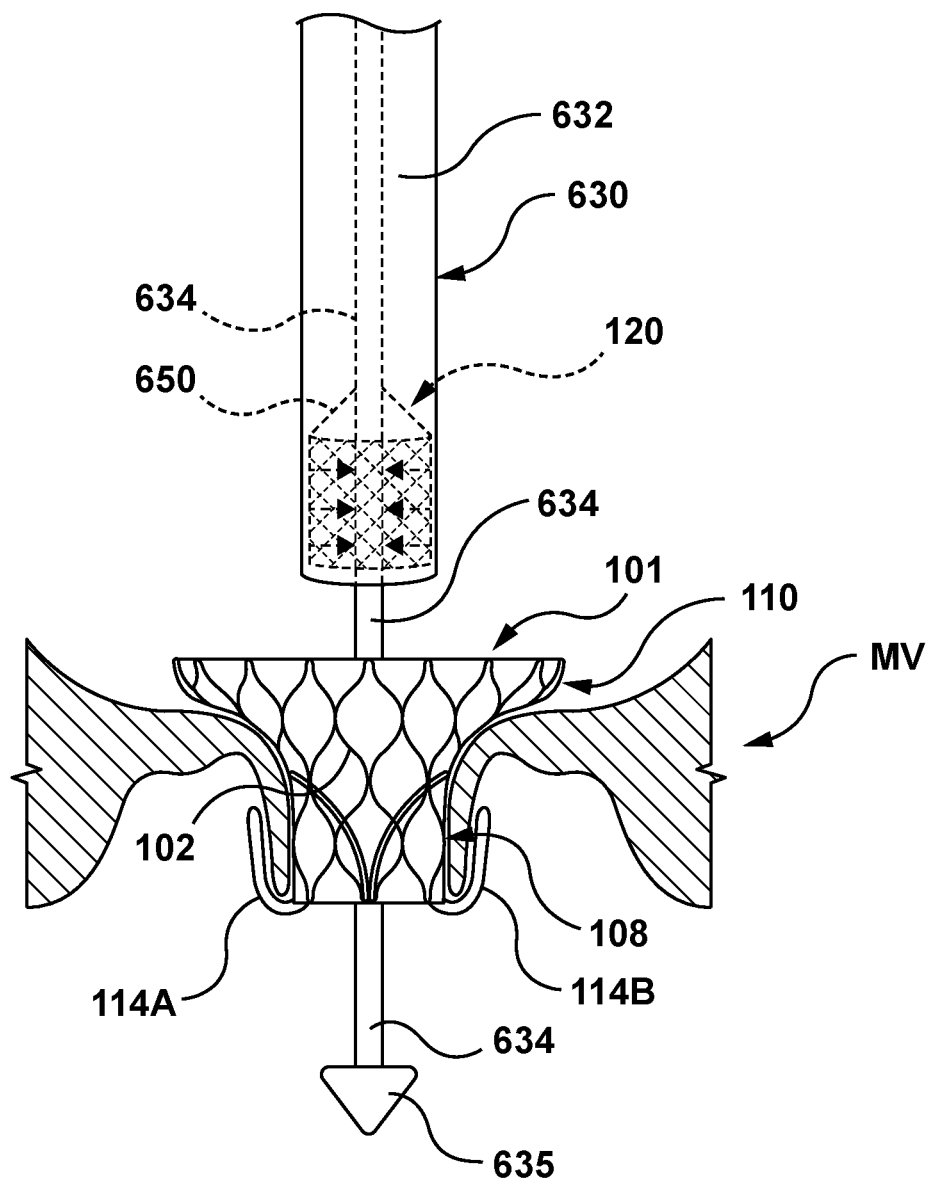
FIG. 6A is a side view illustration of the support flange being delivered within a delivery system to a valve prosthesis after the valve prosthesis has been deployed in situ, wherein the support flange is radially compressed into a delivery configuration within the delivery system.

FIG. 6A is a side view illustration of support flange 120 being delivered within a delivery catheter 630 to valve prosthesis 101 after the valve prosthesis has been deployed and implanted in situ. Delivery catheter 630 may be utilized to deliver support flange 120 concurrently with valve prosthesis 101. If there is a risk of valve prosthesis migration immediately post implantation, then it is advantageous to incorporate the delivery of support flange 120 into the same delivery catheter utilized for delivery of valve prosthesis 101. Delivery catheter 630 includes an outer sheath 632 and an inner tube 634 slidingly disposed therein such that outer sheath 632 and inner tube 634 are moveable relative to each other. Although not required, inner tube 634 may include a tapered distal tip 635 at a distal end thereof for tracking through the vasculature. Although only a distal portion of delivery catheter 630 is shown, it will be understood by those of ordinary skill in the art that both outer sheath 632 and inner tube 634 extend to the proximal end of delivery catheter 630 to be assessable by the clinician. Valve prosthesis 101 in its compressed, delivery configuration (not shown in FIG. 6A) is disposed over a distal portion of inner tube 634 within a distal portion of outer sheath 632 such that outer sheath 632 maintains the valve prosthesis in its compressed configuration when delivery catheter 630 is tracked through a body lumen to the deployment site. Although not required, inner tube 634 may define a lumen therethrough (not shown) for accommodating a guidewire (not shown) therethrough such that inner tube 634 may be advanced over an indwelling guidewire to track delivery catheter 630 to the target site.

During delivery of valve prosthesis 101, support flange 120 is positioned proximal to valve prosthesis 101, disposed over inner tube 634 within outer sheath 632 such that outer sheath 632 maintains both the valve prosthesis and the support flange in their radially compressed configurations when delivery catheter 630 is tracked through a body lumen to the deployment site. Outer sheath 632 is proximally retracted to deploy valve prosthesis 101 and after deployment of valve prosthesis 101, support flange 120 is still radially compressed within outer sheath 632 as shown in FIG. 6A. As shown in FIG. 6A, valve prosthesis 101 is deployed such that first or central portion 108 is disposed in the annulus of the native valve and second or inflow portion 110 having a larger diameter than the central portion engages an upstream side of the annulus to restrict movement of valve prosthesis 101 in a downstream direction of blood flow at the native valve.

Figure 6B:
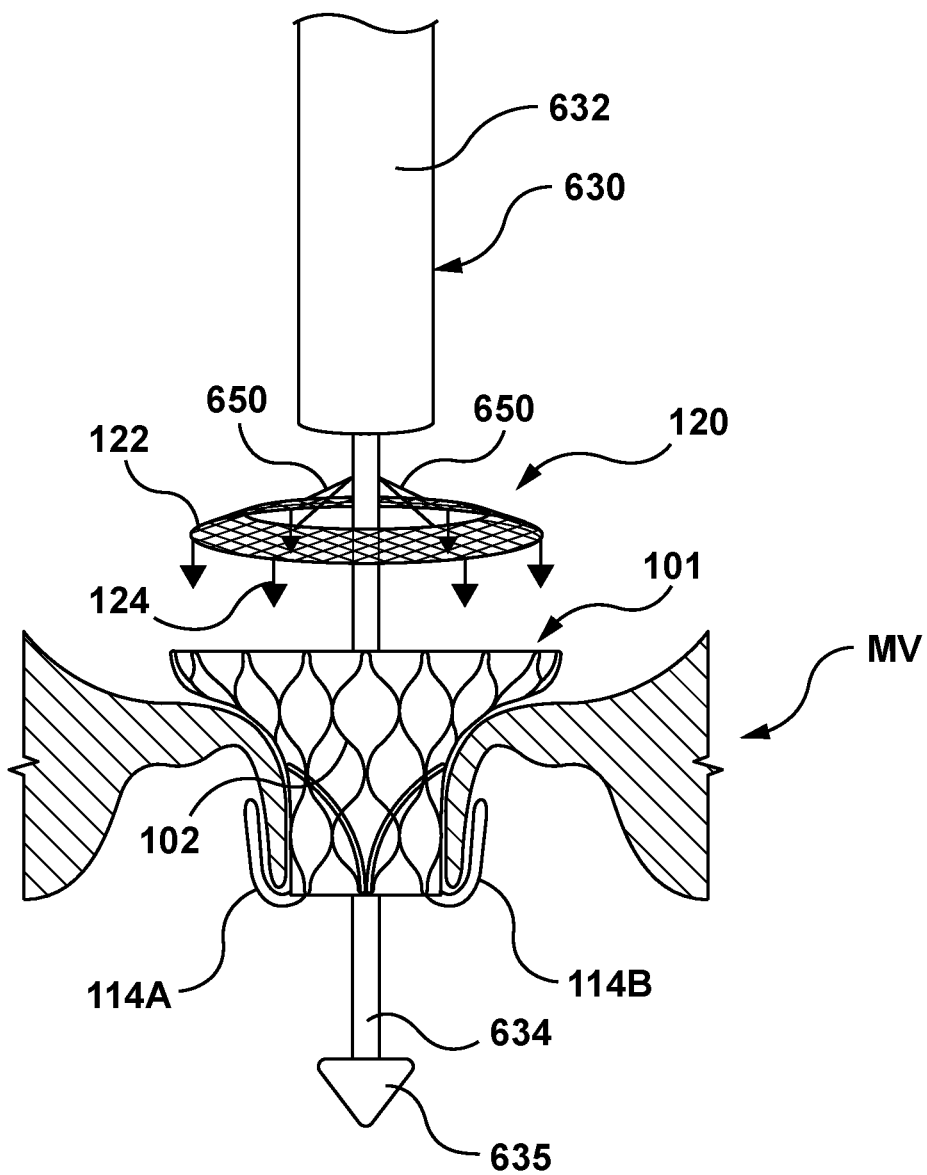
FIG. 6B is a side view illustration of the support flange after being released from the delivery system, wherein the support flange is radially expanded but it not yet attached to the valve prosthesis.

After valve prosthesis 101 has been implanted, support flange 120 is deployed. FIG. 6B is a side view illustration of support flange 120 after being released from outer sheath 632. In FIG. 6B, support flange 120 is radially expanded but is not yet attached to valve prosthesis 101. Outer sheath 632 is proximally retracted to expose support flange 120, thereby permitting support flange 120 to radially expand to its deployed or expanded configuration. In an embodiment hereof, support flange 120 is temporarily coupled or attached to inner tube 634 via one or more sutures or clips 650 so that the support flange is still coupled to the delivery catheter after proximal retraction of outer sheath 632. It is advantageous to have support flange 120 temporarily coupled to the delivery system to give the user more control over the positioning and deployment of the support flange.

Figure 6C:
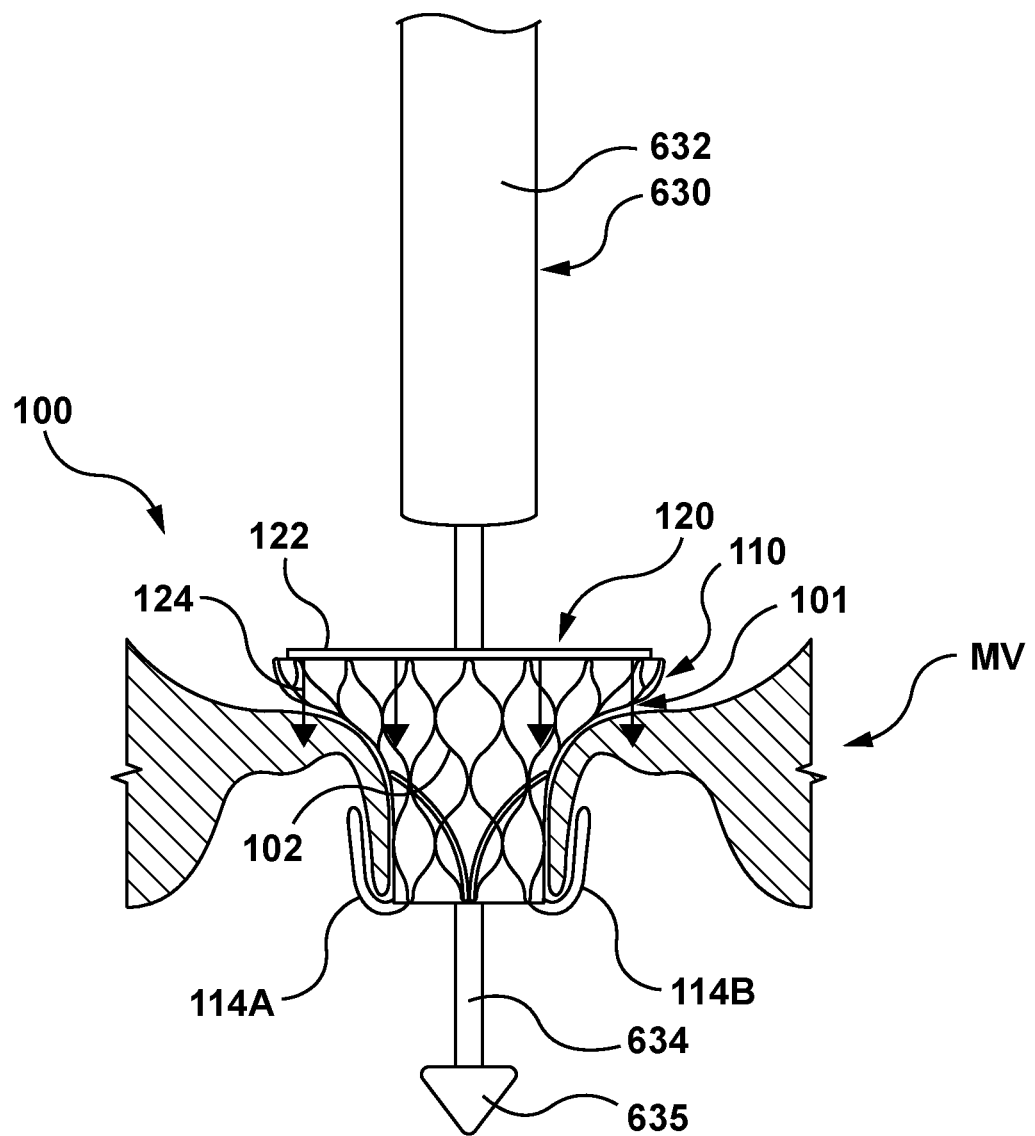
FIG. 6C is a side view illustration of the support flange attached to the valve prosthesis.

After release from outer sheath 632, delivery catheter 630 having support flange 120 still coupled thereto is distally advanced downstream in order to attach support flange 120 to frame 102 of the implanted valve prosthesis. FIG. 6C is a side view illustration of support flange 120 attached to second or inflow portion 110 of valve prosthesis 101 with the plurality of anchors 124. Anchors 124 are configured to embed into the annulus in order to anchor frame 102 of the valve prosthesis to the native valve. Support flange 120 is configured to be located upstream of second or inflow portion 110 of valve prosthesis 101. In this embodiment, anchors 124 extend through the cells or openings 103 of frame 102 (shown in FIG. 1) and into the annulus of the native valve site. Once support flange 120 is secured to the native tissue via anchors 124, support flange 120 may be detached from inner tube 634 and delivery system 630 by cutting sutures or clips 650 or twisting/rotating inner tube 634 to sever the connection between the inner tube and the support flange so that the delivery system may be withdrawn while leaving the support flange in place.

Advantageously, since support flange 120 is a separate component from valve prosthesis 101, support flange 120 may be routinely deployed in order to prevent paravalvular leakage by sandwiching tissue and frame 102 of valve prosthesis 101 together or support flange 120 may only be deployed to topically seal a leak when a leak is identified or observed at the time of implantation of the valve prosthesis. Stated another way, support flange 120 may be utilized in all patients or only in patients where a paravalvular leak is present at the time of implantation. When attached to valve prosthesis 101, support flange 101 serves an anchoring function with active fixation of the valve prosthesis on the atrial side to anchor the valve prosthesis post deployment thereof. In addition support flange 120 also serves a sealing function to prevent or treat paravalvular leakage by providing a continuous circumferential seal around second or inflow portion 110 of valve prosthesis 101 to prevent blood flow between the outer surface or perimeter of valve prosthesis 101 and the native heart valve. Another advantage of separate support flange 120 is that since support flange 120 is deployed after valve prosthesis 101, a functioning valve, i.e., valve prosthesis 101, is in place during deployment of support flange 120 to allow or provide an operator with additional time to work.

Figure 7:
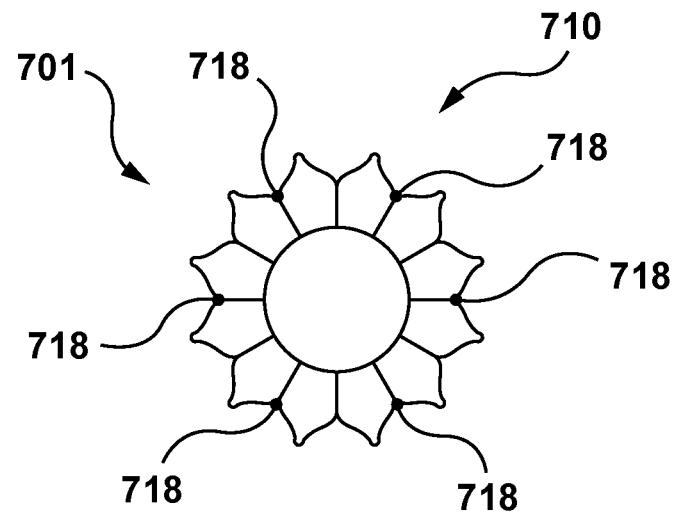
FIG. 7 is a top view illustration of a valve prosthesis according to another embodiment hereof, wherein the valve prosthesis includes a plurality of receiving holes at an inflow end thereof.

In another embodiment hereof depicted in FIG. 7, a valve prosthesis 701 may include a plurality of receiving holes 718 at an inflow end or portion 710 thereof. Valve prosthesis 701 is similar to valve prosthesis 101 with the exception of receiving holes 718. Receiving holes 718 are configured to receive anchors such as anchors 124 described herein. When support flange 120 is deployed and attached to valve prosthesis 701, anchors 124 extend through receiving holes 718 and into the annulus of the native valve site. In order to ensure alignment between anchors 124 of support flange 120 and receiving holes 718, support flange 120 and valve prosthesis 701 are locked into one alignment configuration in the delivery system so that they are also always deployed in the same alignment. Radiopaque markers on the delivery system ensure that the delivery system is not twisted out of alignment during deployment. In an embodiment, receiving holes 718 on valve prosthesis 701 are made from a more radiopaque material than the valve prosthesis to aid alignment with anchors 124 of support flange 120. In another embodiment, valve prosthesis 701 includes radiopaque markers (not shown) that align with similar radiopaque markers on support flange 120 to assist in alignment between the support flange and the valve prosthesis.

Figure 8:
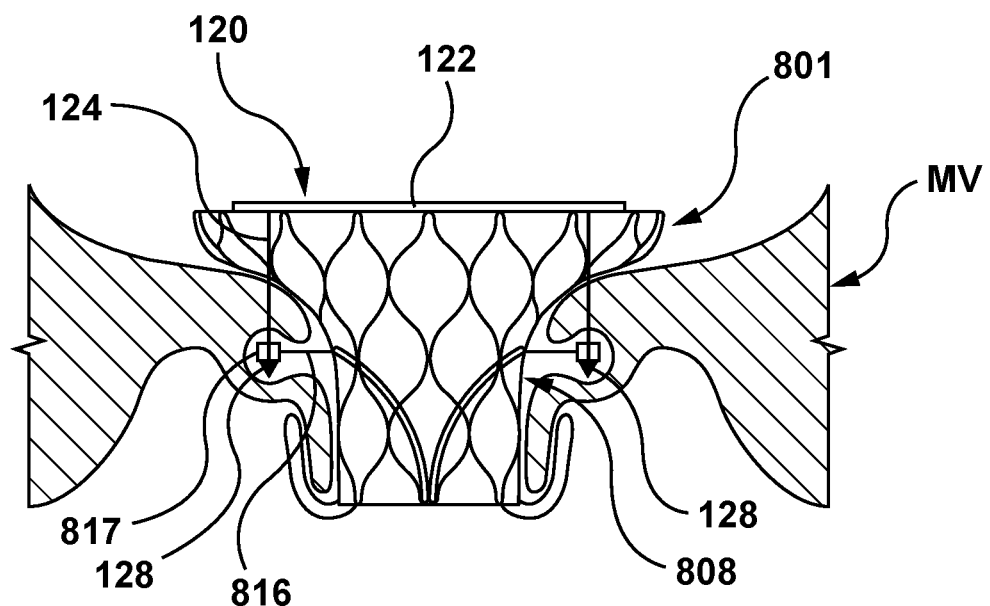
FIG. 8 is a side view illustration of a valve prosthesis according to another embodiment hereof, wherein the valve prosthesis includes a plurality of receiving holes at a central portion thereof and the valve prosthesis is depicted in its deployed or expanded configuration in situ.

In another embodiment depicted in FIG. 8, a first or central portion 808 of a valve prosthesis 801 may include a plurality of receiving arms 816 extending radially outward therefrom. Valve prosthesis 801 is similar to valve prosthesis 101 with the exception of receiving arms 816. Each of the receiving arms 816 includes a respective receiving hole 817, and each of the anchors 124 are configured to engage a respective receiving hole. When support flange 120 is deployed and attached to valve prosthesis 801, anchors 124 extend through the annulus of the native valve site and into receiving holes 817 of receiving arms 816.

In another embodiment hereof, the support flange may be configured to be positioned on the ventricular side of an implanted valve prosthesis. More particularly, FIG. 9 is a perspective view of a support flange 920 according to another embodiment hereof, and FIG. 10 illustrates support flange 920 assembled or attached to a deployed valve prosthesis 101. Support flange 920 is mounted over valve prosthesis 101 pre-deployment and pre-delivery thereof. Support flange 920 is configured to be located downstream of second or inflow portion 110 of valve prosthesis 101 such that support flange 920 encircles first or central portion 108 of valve prosthesis 101.

Similar to support flange 120, support flange 920 has a compressed configuration for delivery within a vasculature and a radially expanded configuration for attachment to frame 102 of valve prosthesis 101. Support flange 920 in the radially expanded configuration is a ring 922 defining a central opening 925 therethrough. In an embodiment hereof, ring 922 is oval or oblong shaped in the expanded configuration to accommodate native valve tissue adjacent to first or central portion 108 of valve prosthesis 101. "Oval or oblong" as utilized herein includes a structure that has a rectangular shape or configuration, with angular or rounded corners, as well as an oval or other rounded shape or configuration. Narrowed portions 952 of ring 922 are configured to be circumferentially aligned with leaflets of the native valve and elongated portions 954 of ring 922 are configured to be circumferentially offset from the leaflets of the native valve. Ring 922 has an upstream surface 921 and an opposing downstream surface 923. Ring 922 is formed from a shape memory or self-expanding material to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein.

In the embodiment of FIG. 9, a plurality of anchors 924 are attached to ring 922 and extend from upstream surface 921 of ring 922 in an upstream direction from ring 922. Similar to anchors 124, each anchor 924 includes a shaft 926 with a pointed tip, barb or clip 928 at an unattached end thereof to embed or press into the native anatomy. Anchors 924 are configured to embed into the annulus in order to anchor frame 102 of the valve prosthesis to the native valve. In an embodiment, anchors 924 extend through the annulus of the native valve site and into the cells or openings 103 of frame 102 (shown in FIG. 1) in order to attach support flange 920 to frame 102. In another embodiment, the inflow portion of frame 102 may include receiving holes similar to receiving holes 718 described above, and anchors 924 extend through the annulus of the native valve site and into the receiving holes of frame 102 in order to attach support flange 920 to frame 102.

Figure 11:
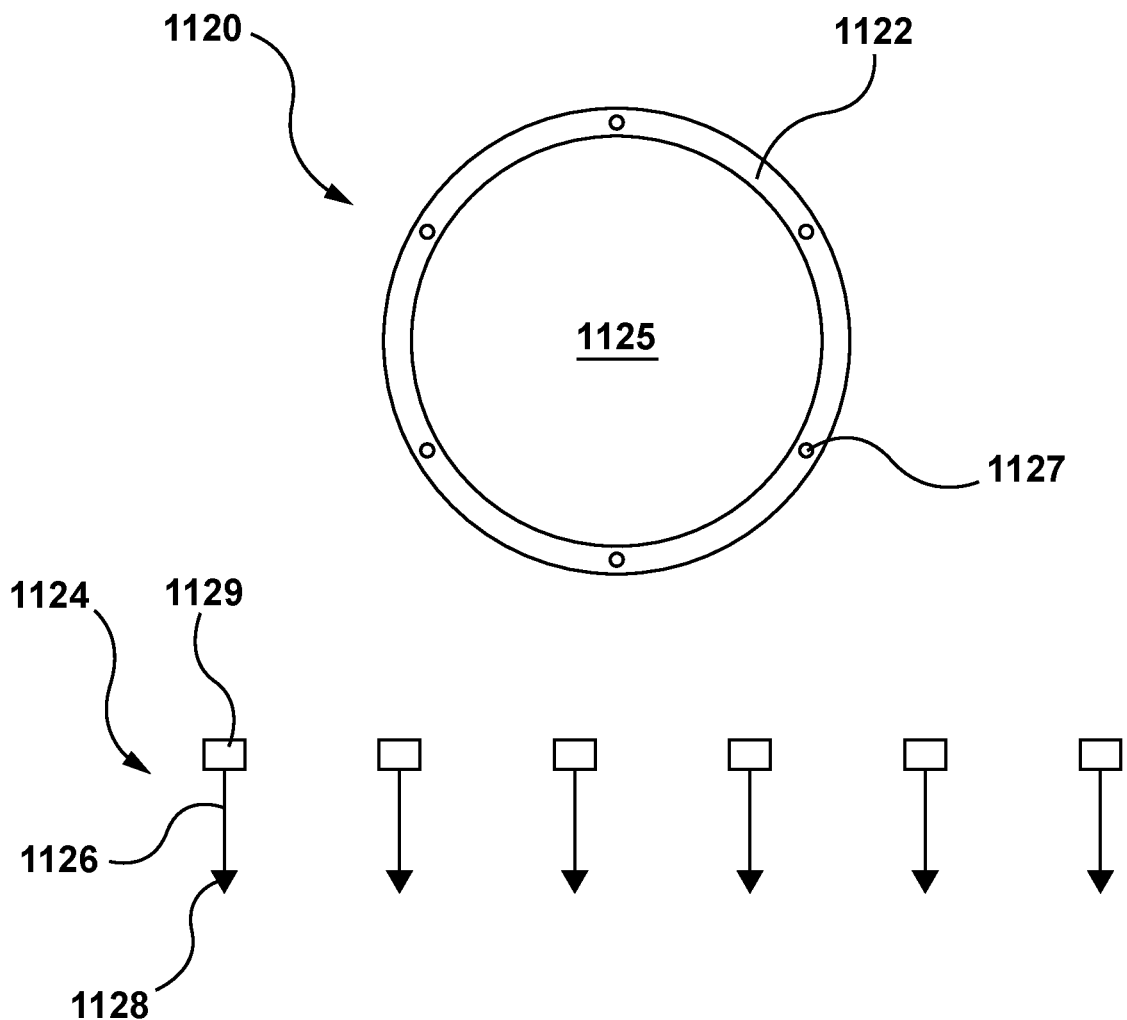
FIG. 11 is an exploded view of a support flange and a plurality of anchors according to another embodiment hereof, wherein the support flange is configured to be attached to a valve prosthesis after the valve prosthesis has been deployed in situ and the plurality of anchors are separate from or unattached to the support flange.
Figure 12:
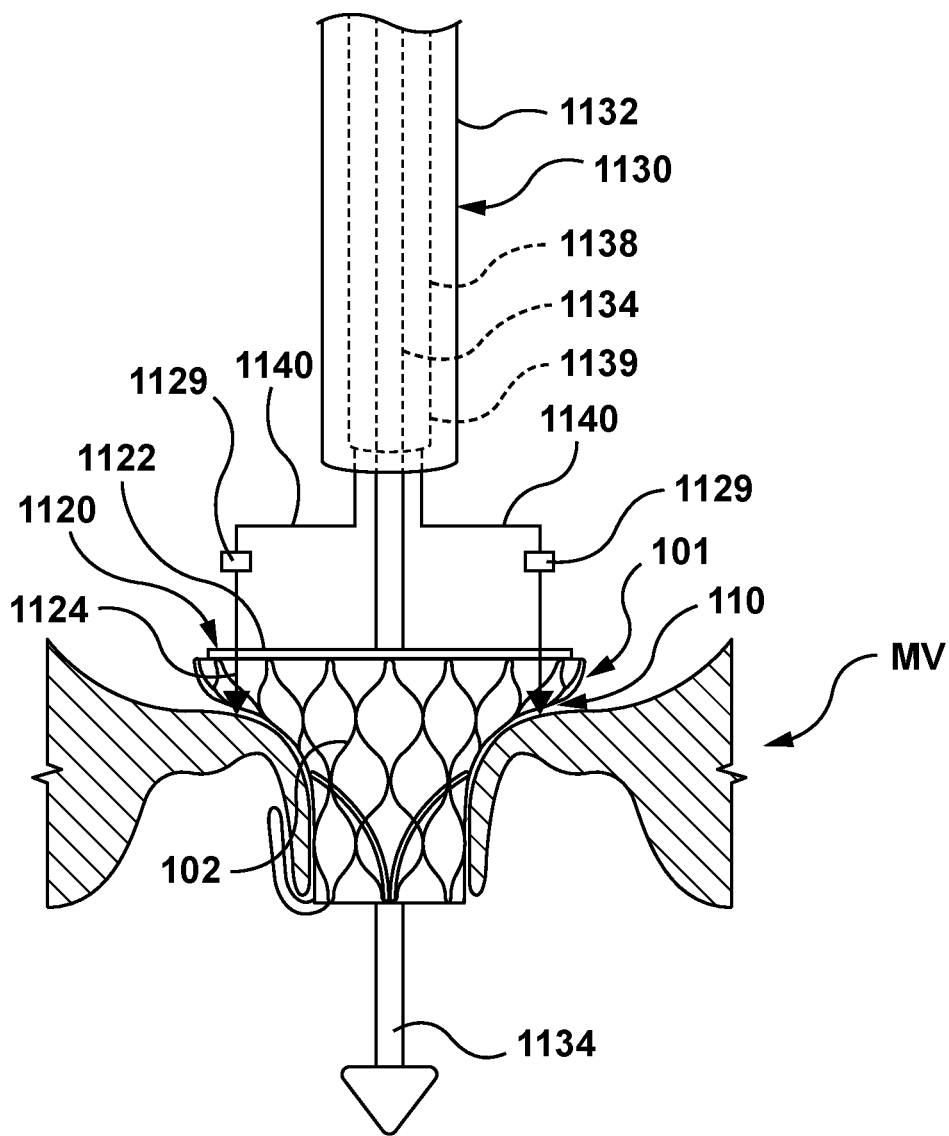
FIG. 12 is a side view illustration of the support flange and the plurality of anchors of FIG. 11 being delivered to a deployed valve prosthesis.

In another embodiment hereof, the plurality of anchors or pins configured to attach the support flange to the frame of the valve prosthesis and to embed into the annulus to anchor the frame of the valve prosthesis to the native valve may be separate from or unattached to the support flange. More particularly, FIG. 11 is an exploded view of a support flange 1120 and a plurality of anchors 1124. FIG. 12 is a side view illustration of support flange 1120 and anchors 1124 being delivered to a deployed valve prosthesis. Similar to the embodiments described above, support flange 1120 has a compressed configuration for delivery within a vasculature and a radially expanded configuration for attachment to frame 102 of valve prosthesis 101. In this embodiment, support flange 1120 in the radially expanded configuration is a ring 1122 defining a central opening 1125 therethrough but support flange 1120 may alternatively be an annular component having a mesh or lattice configuration as described above. Ring 1122 is formed from a shape memory or self-expanding material to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein. Unlike the embodiments described above, ring 1122 also includes a plurality of guide holes 1127 configured to receive anchors 1124. Guide holes 1127 may be equally spaced around ring 1122 as shown in FIG. 11, or may be in any other suitable pattern or spacing.

Each anchor 1124 includes a shaft 1126 with a pointed tip, barb or clip 1128 at an end thereof to embed or press into the native anatomy. Although not required, an opposing end of each anchor 1124 may also include a stopper 1129. After support flange 1120 is deployed and positioned adjacent to second or inflow end 110 of valve prosthesis 101 as shown in FIG. 12, anchors 1124 are delivered to extend through guide holes 1127 of support flange 1120 and into the annulus of the native valve site. Enlarged ends or stoppers 1129 of anchors 1124 prevent anchors 1124 from passing through guide holes 1127.

In order to deliver anchors 1124 into guide holes 1127, a delivery catheter includes a plurality of radially expandable push wires. More particularly, a delivery catheter 1130 for delivering support flange 1120 and anchors 1124 is illustrated in FIG. 13. FIG. 13 is a sectional side view of a distal end portion of intermediate shaft 1138 of delivery catheter 1130 with a plurality of radially expandable push arms 1140 and the plurality of anchors 1124 housed therein during delivery thereof. Intermediate shaft 1138 is removed from delivery catheter 1130 in FIG. 13 for illustrative purposes only. FIG. 13A is a cross-sectional view taken along line A-A of FIG. 13. FIG. 14 is a sectional side view of the distal end portion of intermediate shaft 1138 with anchors 1124 being deployed via the plurality of radially expandable push wires 1140.

Delivery catheter 1130 is similar to delivery catheter 630 except that delivery catheter 1130 includes an intermediate shaft 1138 for housing the plurality of radially expandable push wires 1140 and anchors 1124. More particularly, delivery catheter 1130 includes an outer sheath 1132, intermediate shaft 1138, and inner tube 1134 slidingly disposed therein such that outer sheath 1132 is moveable relative to each of the intermediate shaft and the inner tube. Although only a distal portion of delivery catheter 1130 is shown, it will be understood by those of ordinary skill in the art that outer sheath 1132, intermediate shaft 1138, and inner tube 1134 extend to the proximal end of delivery catheter 1130 to be assessable by the clinician. Valve prosthesis 101 in its compressed, delivery configuration is disposed over a distal portion of inner tube 1134 within a distal portion of outer sheath 1132 such that outer sheath 1132 maintains the valve prosthesis in its compressed configuration when delivery catheter 1130 is tracked through a body lumen to the deployment site. Although not required, inner tube 1134 may define a lumen therethrough (not shown) for accommodating a guidewire (not shown) therethrough such that inner tube 1134 may be advanced over an indwelling guidewire to track delivery catheter 1130 to the target site.

In this embodiment, each radially expandable push wire 1140, when expanded or deployed, is configured to radially align an anchor 1124 coupled to an end of the push wire with a guide hole 1127 of support flange 1120. FIGS. 15-17 described herein illustrate exemplary configurations for temporarily coupling each anchor 1124 to its respective push wire 1140. Although shown with six push wires circumferentially spaced apart, a greater number of push wires or a fewer number of push wires may be used depending upon application and the number of anchors. Each radially expandable push wire 1140 is an individual or separate strand or filament having at least a distal portion thereof formed from a self-expanding material and shape-set in the deployed or expanded configuration shown in FIGS. 12 and 14.

Intermediate shaft 1138 is shorter than outer sheath 1132, with a distal end 1139 positioned proximal to support flange 1120 during delivery thereof. As best shown in FIGS. 13 and 13A, which illustrate intermediate shaft 1138 removed from delivery catheter 1130 for illustrative purposes only, intermediate shaft 1138 includes a plurality of lumens 1137 formed in a sidewall thereof for housing or receiving push wires 1140 and anchors 1124. Although intermediate shaft 1138 is shown with six lumens circumferentially spaced apart, it will be understood by one of ordinary skill in the art that the number of lumens corresponds to the number of push wires utilized therein, which may vary according to application as described above. Push wires 1140 are slidingly positioned within lumens 1137, and push wires 1140 may be moved relative to intermediate shaft 1138 is in order to selectively deploy or expand the distal portions of push wires 1140.

Support flange 1120 is delivered and deployed similar to support flange 120 described above. More particularly, during delivery of valve prosthesis 101 support flange 1120 is positioned proximal to valve prosthesis 101, disposed over inner tube 1134 within outer sheath 1132 such that outer sheath 1132 maintains both the valve prosthesis and the support flange in their radially compressed configurations when delivery catheter 1130 is tracked through a body lumen to the deployment site. As previously stated, distal end 1139 of intermediate shaft 1138 is proximal to support flange 1120. During delivery of delivery catheter 1130, each push wire 1140 is compressed into a delivery configuration in which the entire length of each push wire is housed within its respective lumen 1137 of intermediate shaft 1138. When in its compressed or delivery configuration, the distal portion of each push wire 1140 has a straightened profile that is enclosed within one of lumens 1137 formed in the sidewall of intermediate shaft 1138 as shown in FIG. 13.

Outer sheath 1132 is proximally retracted to deploy valve prosthesis 101 and after deployment of valve prosthesis 101, support flange 1120 is still radially compressed within outer sheath 1132. Outer sheath 1132 is further proximally retracted to deploy support flange 1120 similar to support flange 120 described above. Similar to support flange 120, support flange 1120 may be temporarily coupled or attached to inner tube 1134 via one or more sutures or clips (not shown) so that the support flange is still coupled to the delivery catheter after proximal retraction of outer sheath 1132. After release from outer sheath 1132, delivery catheter 1130 having support flange 1120 still coupled thereto is advanced downstream in order to position support flange 120 adjacent to frame 102 of the implanted valve prosthesis.

With support flange 120 positioned adjacent to frame 102 of the implanted valve prosthesis, push wires 1140 and anchors 1124 coupled thereto are then distally advanced downstream towards support flange 120 by the user such that the distal portions of push wires 1140 are exposed or extend out of intermediate shaft 1138 and the distal portion of each push wire 1140 is permitted to self-expand to their shape-set deployed or expanded configuration in which the distal portion of each push wire has a stepped profile as shown in FIG. 14. Push wires 1140 may be simultaneously deployed at the same time, or may be individually deployed as needed. Push wires 1140 and anchors 1124 coupled thereto are aligned with support flange 1120 using radiopaque markers (not shown) on the implanted valve prosthesis. The shape-set deployed or expanded configuration of push wires 1140 have the same diameter as the implanted valve prosthesis to aid alignment. Radiopaque markers on the delivery system ensure the same central axis is maintained throughout the procedure.

Push wires 1140 and anchors 1124 coupled thereto are further distally advanced downstream until anchors 1124 contact support flange 1120 and anchors 1124 extend through guide holes 1127 of support flange 1120. Anchors 1124 embed into the annulus in order to anchor frame 102 of the valve prosthesis to the native valve. After anchors 1124 extend through guide holes 1127 of support flange 1120, anchors 1124 are embedded and secured to the native tissue and push wires 1140 may be detached from anchors 1124 by proximally retracting the push wires. Push wires 1140 are proximally retracted by the user such that the distal portions thereof are pulled back into their respective lumen 1137 of intermediate shaft 1138. Once support flange 1120 is secured to the native tissue via anchors 1124 and push wires 1140 have been recaptured, support flange 1120 may be detached from inner tube 1134 and delivery system 1130 by cutting the suture or clip or twisting/rotating inner tube 1134 to sever the connection between the inner tube and the support flange so that the delivery system may be withdrawn while leaving the support flange in place.

FIGS. 15-17 illustrate exemplary configurations for temporarily coupling each anchor to its respective push wire. FIG. 15 is a side view of an anchor 1524 having a stopper or proximal end 1529 which is temporarily coupled to a distal end 1560 of its respective push wire via a ball and socket-type joint. Distal end 1560 of the push wire include a socket 1562 with a split opening 1568. Anchor 1524 includes barb 1528 at its distal end and a ball 1566 at its proximal end, with ball 1566 being configured to be received within a housing 1564 defined by socket 1562. As best shown in the perspective view of socket 1562 shown in FIG. 16, split opening 1568 includes a plurality of slits 1570 that partially extend over or cover split opening 1568 so that split opening 1568 is relatively deformable to allow or permit ball 1566 of anchor 1524 to pull free or detach when desired. Such a split opening design allows a large push force to be applied to anchor 1524 but does not lead to a high detachment force. The detachment force required to pull ball 1566 free of socket 1562 is less than the force it would take to pull anchor 1524 free of the tissue. In the embodiment depicted in FIG. 17, a ball 1766 of an anchor 1724 includes a key or extension 1772 on a proximal end thereof to prevent rotation thereof when a push force is applied thereto. A distal end 1760 of the push wire include a socket 1762 defining a housing 1764 configured for receiving ball 1766. Socket 1762 includes a mating receptacle 1774 for receiving key or extension 1772 of ball 1766 to prevent rotation the anchor when a push force is applied thereto and thereby to provide additional stability when pushing anchor 1724 into the tissue.

Although support flanges described herein are concurrently delivered with the delivery catheter utilized to deliver and deploy the valve prosthesis, in another embodiment hereof a separate deliver catheter may be utilized to subsequently deliver a support flange to a previously implanted valve prosthesis in order to improve anchorage of the previously implanted valve prosthesis and prevent and/or repair paravalvular leakage of the previously implanted valve prosthesis. A support flange may be delivered and implanted post implantation of the valve prosthesis on an as-needed basis.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A valve prosthesis assembly configured for transcatheter implantation into a native valve site, the valve prosthesis assembly comprising:
   a valve prosthesis having a compressed configuration for delivery within a vasculature and a radially expanded configuration for deployment within an annulus of the native valve site, the valve prosthesis including,
      a prosthetic valve component, and
      a frame including
         a central portion supporting the prosthetic valve component, the central portion configured to fit within an annulus of the native valve site, and
         an inflow portion configured to engage an upstream side of the annulus and restrict movement of the valve prosthesis in a downstream direction of blood flow at the native valve site;
   a separate support flange configured to be attached to the frame after the valve prosthesis has been deployed in situ, wherein the support flange is configured to be located upstream of the inflow portion of the frame; and
   a plurality of anchors configured to attach the support flange to the frame and configured to embed into the annulus to anchor the frame of the valve prosthesis to the native valve.

2. The valve prosthesis assembly of claim 1, wherein the inflow portion further includes receiving holes configured to receive the anchors.

3. The valve prosthesis assembly of claim 2, wherein the anchors are attached to the support flange and extend in a downstream direction from the support flange, wherein the anchors are configured to extend through the receiving holes and into the annulus of the native valve site.

4. The valve prosthesis assembly of claim 2, wherein the support flange includes guide holes, wherein the anchors are separate from the support flange and are configured to extend into the guide holes, the receiving holes, and into the annulus in situ.

5. The valve prosthesis assembly of claim 1, wherein the central portion of the frame includes receiving arms extending radially outward therefrom, wherein each of the receiving arms includes a respective receiving hole,
wherein each of the anchors are configured to engage a respective receiving hole.

6. The valve prosthesis assembly of claim 5, wherein the anchors are attached to the support flange and extend downstream to engage the receiving holes.

7. The valve prosthesis assembly of claim 1, wherein the support flange has a compressed configuration for delivery within a vasculature and a radially expanded configuration for attachment to the frame.

8. The valve prosthesis assembly of claim 7, wherein the support flange in the radially expanded configuration is an annular component having an outer diameter and an inner diameter that defines a central opening therethrough, the annular component being substantially planar.

9. The valve prosthesis assembly of claim 8, wherein the annular component has a mesh configuration with a plurality of openings defined by a framework of the mesh configuration, and the central opening and the plurality of openings are oriented transverse to blood flow when the support flange is in the radially expanded configuration in situ.

10. A valve prosthesis assembly configured for transcatheter implantation into a native valve site, the valve prosthesis assembly comprising:
a valve prosthesis having a compressed configuration for delivery within a vasculature and a radially expanded configuration for deployment within an annulus of the native valve site, the valve prosthesis including
a prosthetic valve component, and
a frame including
a central portion supporting the prosthetic valve component, the central portion configured to fit within the annulus when the valve prosthesis is in the radially expanded configuration, and
an inflow portion having a larger diameter than the central portion when the valve prosthesis is in the radially expanded configuration to engage an upstream side of the annulus and restrict movement of the valve prosthesis in a downstream direction of blood flow at the native valve site;
a separate support flange configured to be attached to the frame after the valve prosthesis has been deployed in situ, the support flange having a compressed configuration for delivery within a vasculature and a radially expanded configuration for attachment to the frame, wherein the support flange in the radially expanded configuration is a ring defining an opening therethrough and wherein the support flange is formed from a shape memory material and wherein the support flange is configured to be located upstream of the inflow portion of the frame; and
a plurality of anchors configured to attach the support flange to the frame and configured to embed into the annulus to anchor the frame of the valve prosthesis to the native valve.

11. The valve prosthesis assembly of claim 10, wherein the valve prosthesis further includes receiving holes configured to receive the anchors.

12. The valve prosthesis assembly of claim 11, wherein the anchors are attached to the support flange and are configured to extend through the receiving holes.

13. The valve prosthesis assembly of claim 12, wherein the support flange includes guide holes, and wherein the anchors are separate from the support flange and are configured to extend through the guide holes and the receiving holes.

14. The valve prosthesis assembly of claim 10, wherein the ring is substantially planar.

15. The valve prosthesis assembly of claim 14, wherein the opening is a central opening and the ring has a mesh configuration with a plurality of openings defined by a framework of the mesh configuration, and the central opening and the plurality of openings are oriented transverse to blood flow when the support flange is in the radially expanded configuration in situ.

16. A method of delivering and deploying a valve prosthesis assembly within a native valve via transcatheter implantation, the method comprising the steps of:
advancing a valve prosthesis within a vasculature to the native valve, wherein the valve prosthesis includes a prosthetic valve component coupled to a central portion of a frame and wherein the valve prosthesis is in a compressed configuration for delivery;
deploying the valve prosthesis to a radially expanded configuration such that the central portion is disposed in the annulus of the native valve and an inflow portion having a larger diameter than the central portion engages an upstream side of the annulus to restrict movement of the valve prosthesis in a downstream direction of blood flow at the native valve;
after the valve prosthesis has been deployed, delivering a support flange to the native valve;
deploying the support flange upstream of the inflow portion of the frame; and
attaching the support flange to the frame of the valve prosthesis with a plurality of anchors, wherein the anchors are configured to embed into the annulus in order to anchor the frame of the valve prosthesis to the native valve.

17. The method of claim 16,
wherein the anchors extend from a downstream surface of the support flange,
wherein the inflow portion further includes receiving holes configured to receive the anchors,
wherein the step of deploying the support flange includes aligning the anchors with the receiving holes, and
wherein the step of anchoring the support flange to the frame includes advancing the support flange downstream such that the anchors extend through the receiving holes and into the annulus.

18. The method of claim 16,
wherein the support flange includes guide holes therethrough,
wherein the inflow portion includes receiving holes configured to receive anchors,
wherein the step of deploying the support flange includes aligning the guide holes with the receiving holes, and
wherein the anchors are separate from the support flange and the step of anchoring the support flange to the frame includes advancing the anchors through the guide holes of the support flange, through the receiving holes of the inflow portion, and into the annulus in situ.

19. The method of claim 18, wherein advancing the anchors through the guide holes of the support flange includes advancing a respective push wire in order to individually advance each anchor, each push wire individually associated with a respective anchor and each push wire having a shape memory shape with a radially expanded step therein.

20. The method of claim 16,
wherein the anchors extend from a downstream surface of the support flange,
wherein the central portion of the frame includes receiving arms extending radially outward therefrom, wherein each of the receiving arms includes a respective receiving hole configured to receive a respective anchor,
wherein the step of deploying the support flange includes aligning the anchors with the receiving holes, and
wherein the step of anchoring the support flange to the frame includes advancing the support flange downstream such that the anchors extend through the receiving holes.

* * * * *